United States Patent
Schweiger (10) Patent No.: US 8,444,594 B2
(45) Date of Patent: May 21, 2013

(54) SYSTEM FOR REMOVAL AND INFUSION OF BODY FLUID, AND METHOD FOR ITS OPERATION

(75) Inventor: Gerd Schweiger, St. Stefan (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 505 days.

(21) Appl. No.: 12/680,010

(22) PCT Filed: Sep. 26, 2008

(86) PCT No.: PCT/EP2008/008228
§ 371 (c)(1),
(2), (4) Date: May 25, 2010

(87) PCT Pub. No.: WO2009/043555
PCT Pub. Date: Apr. 9, 2009

(65) Prior Publication Data
US 2010/0268118 A1  Oct. 21, 2010

(30) Foreign Application Priority Data
Sep. 27, 2007 (EP) ..................... 07019012

(51) Int. Cl.
*A61M 1/00* (2006.01)
*F16K 5/00* (2006.01)
*A61B 5/15* (2006.01)

(52) U.S. Cl.
USPC .............. 604/32; 604/248; 251/304; 600/573

(58) Field of Classification Search
USPC ................. 604/4.01, 6.1, 32, 167.03, 167.05, 604/248, 335; 251/304, 158, 160, 187–188, 251/192; 137/625.46, 625.47
See application file for complete search history.

(56) References Cited

U.S. PATENT DOCUMENTS

| 3,834,372 A * | 9/1974 | Turney .................... 600/561 |
| 4,573,968 A | 3/1986 | Parker |
| 4,608,996 A | 9/1986 | Brown |
| 4,738,265 A * | 4/1988 | Ritchart et al. ............. 600/486 |
| 5,104,387 A * | 4/1992 | Pokorney et al. ........... 604/248 |
| 5,135,026 A * | 8/1992 | Manska ...................... 137/555 |

(Continued)

FOREIGN PATENT DOCUMENTS
EP 0513789 11/1992
FR 2535848 5/1984

(Continued)

OTHER PUBLICATIONS

International Search Report for PCT/EP2008/008228 completed Oct. 30, 2008.

*Primary Examiner* — Quynh-Nhu H Vu
(74) *Attorney, Agent, or Firm* — Barnes & Thornburg LLP (57) ABSTRACT

The invention relates to a system for the extraction and infusion of a body fluid, in particular a system for the extraction and infusion of blood, having a fluid distribution device with an outer structural element at which several connection ports are formed and an inner structural element which is arranged, at least partially, in a seat in the outer structural element, is displaceable between positions and has a hollow space configured for the intake and discharge of a fluid. The invention also relates to a method for operating a system for the extraction and infusion of a body fluid.

10 Claims, 9 Drawing Sheets

U.S. PATENT DOCUMENTS

| | | | |
|---|---|---|---|
| 5,165,406 A | 11/1992 | Wong | |
| 5,466,228 A | 11/1995 | Evans | |
| 5,529,758 A * | 6/1996 | Houston | 422/171 |
| 5,613,511 A * | 3/1997 | Andersen et al. | 134/167 R |
| 5,758,643 A | 6/1998 | Wong et al. | |
| 6,017,451 A * | 1/2000 | Kopf | 210/232 |

FOREIGN PATENT DOCUMENTS

| | | |
|---|---|---|
| GB | 1512989 | 6/1978 |
| WO | WO91/18632 | 12/1991 |
| WO | WO2006/039310 | 4/2006 |
| WO | WO2007/137285 | 11/2007 |

* cited by examiner

SYSTEM FOR REMOVAL AND INFUSION OF BODY FLUID, AND METHOD FOR ITS OPERATION

This patent application is a U.S. national counterpart of international application serial no. PCT/EP2008/008228 filed on Sep. 26, 2008, which claims priority to European Patent Application No. 07019012.9 filed on Sep. 27, 2007.

BACKGROUND INFORMATION RELATING TO THE INVENTION

Fluid collection systems are used, for example, in the fields of medicine and laboratory- or analytical technologies. One example finds application in systems which serve to collect a sample of a body fluid together with an optional analysis of the collected sample in an analytical equipment appropriate for the purpose. In particular, such systems are used to collect blood from a patient and to analyze at least a portion of the collected blood in blood analysis equipment. In this connection it can also be arranged that the collection of blood takes place automatically on a continuous basis. Furthermore, the collection technique can be applied to arterial—as well as venous blood. A subsequent analysis of the blood is then carried out to obtain treatment-relative information about the condition of the patient and thereby facilitate specific treatment and therapy. With the assistance of suitable analytical equipment different blood parameters can be examined—for example, the partial pressure of oxygen and carbon dioxide as well as the degree of oxygen saturation. Other parameters are the pH-value, the haematocrit value or the contents of sodium, calcium or potassium.

Such systems are combined to collect a sample of the body fluid, for example, a blood sample and they are often provided with system components for carrying out an infusion, where the infusion is capable of either being coupled with the analysis of the sample of collected body fluid—or not. In such a system, it is possible to integrate components such as a three-way valve into fluid distribution tubing between the patient and items of equipment being used to his advantage and comprising, in particular, the analytical equipment and an infusion device. With these components it is possible to influence as becomes necessary the stream of body fluids flowing in the distribution tubing connecting the patient with the relevant items of equipment.

In connection with a system for collection and infusion, the need often arises to vary the rate of flow of the infusion solution being fed to the patient through distribution tubing. By reversing the direction of flow, blood can be collected from the patient. A distribution device in the distribution tubing system serves to prepare a sample of blood which can be subsequently examined with the help of analytical equipment. Once the sample has been taken, a further reversal of direction of flow allows the infusion to be continued. Incidentally, this also permits blood residues to be cleaned out of the fluid distribution tubing.

In the case of devices used for collecting a sample of a body fluid, the use of a septum is known. In such a situation, the sample is collected from the distribution tubing by means of a capillary or needle, which is used to penetrate the septum so that the tip of the capillary or needle inside the tubing comes into contact with the body fluid. After the sample has been collected by means of the capillary or needle, the latter is withdrawn again out of the septum. To ensure sterility, the capillary or needle must be sterilized each time before a sample is taken or a new one-time unit must be used each time. In such situations, problems arise because it is necessary to protect both outer sides of the septum against contamination between two sample-taking methods.

It is further known that a body fluid sample can be taken out of fluid distribution tubing by means of an over-pressure valve. The sample collected in this way can be conducted to the desired analytical instrument. Optionally, a three-way valve can also be inserted. When the over-pressure valve is opened, this system presents a direct fluid connection between the distribution tubing of the analytical equipment and the patient. This constitutes an inherent safety risk. Furthermore, problems have been encountered in practice with the valve seal, which means that it is difficult to satisfy the high requirements placed upon the over-pressure valve to function as a sterile barrier between the patient and the analytical equipment. A three-way valve for fluids having 3 positions is known from the document U.S. Pat. No. 4,608,996. In each of the three positions a fluid connection is provided between precisely two of the three external connection ports, namely a sampling port, a patient port, and an outlet port.

A method and a device for monitoring blood chemistry are known from U.S. Pat. No. 5,758,643. The system makes it possible to monitor blood gases and electrolytes. It can collect blood from the circulation of the patient by means of a catheter and pump. The construction of the analytical equipment includes several sensors to determine the different parameters. This unit is located very close to the patient catheter. Following completion of the analysis, the remaining collected blood is returned and the system is rinsed with infusion liquid. An internal monitoring method permits the patient to be connected to the analyzing equipment with connecting tubing of varying lengths and different flow volume capacities.

Furthermore, there is known from U.S. Pat. No. 5,165,406 a sensing arrangement for a combined infusion- and blood analysis system. One sensing arrangement exhibits an electrode arrangement which is mounted in an electrode space.

From the document WO 2007/137285 A2, there is known a valve device in which a structural element containing a hollow space is mounted pivotably such that the hollow space can be brought into fluid connection with two openings formed in the housing in two rotation positions, respectively. Three of the openings located in the housing are provided with connection ports to which the fluid distribution tubing can be coupled.

Document WO 91/18632 describes a valve apparatus in which optionally two separated fluid connection pairs can be connected by means of a hollow space within an inner structural element. The hollow space is formed such that an inlet connection port can be connected alternatively with two outlets.

The document U.S. Pat. No. 3,834,372 discloses a valve apparatus where four connection ports are formed with the opposite connections lying in pairs. In different valve positions, adjacent or opposing connection ports can be connected through a hollow space.

A valve apparatus is also described in the document U.S. Pat. No. 5,466,228 in which an inner structural element is mounted pivotably in a housing which itself has several connection ports in order to connect pairs of connection ports.

The hollow space is of such a design that in certain positions adjacent connection ports in the housing are connected together.

SUMMARY OF THE INVENTION

It is against the above background that the present invention provides certain unobvious advantages and advancements over the prior art. In particular, the inventor has recognized a need for improvements in a system for the extraction and infusion of a body fluid and method for operating the same. Although the present invention is not limited to specific advantages or functionality, it is noted that the present invention provides a system for the extraction and infusion of a body fluid having a fluid distribution device and a method for operating the system, which, even when used frequently, allows a body fluid sample to be extracted reliably, and which, depending on the purpose of the application, allows the sample to be safely extracted or distributed as desired. Furthermore, the preservation of a high level of sterility shall to be possible.

In accordance with one embodiment of the present invention, the invention comprises the concept of a system for the extraction and infusion of a body fluid, in particular a system for the extraction and infusion of blood, having a fluid distribution device having an outer structural element at which several connection ports are formed and an inner structural element which, at least partially, is arranged within a seat in the outer structural element, is displaceable between positions and has a hollow space configured for the intake and discharge of a fluid, wherein:

at the fluid distribution system a first connection port as patient-side connection port, a first assigned connection port which is assigned to the first connection port as infusion-side connection port and a second connection port as an analyzer-side connection port are formed, in a first position of the inner structural element a first bi-directional fluid connection through the hollow space is formed between the first connection port and the first assigned connection port with the hollow space being separated from the second connection port and a second assigned connection port, which is assigned to the second connection port, and in a second position a second bi-directional liquid connection is formed through the hollow space between the second connection port and the second assigned connection port with the hollow space being separated from the first connection port and the first assigned connection port.

A body fluid of the patient, in particular blood, reaches the fluid distribution device, namely the hollow space, through the patient-side connection port. If the system is used to administer an infusion, the patient-side connection port also serves to feed an infusion fluid supplied through the infusion-side connection port into the tubing to the patient. The connection port to the analyzing equipment serves to discharge an extracted sample to an analyzing apparatus and, if required, through a suitable tubing system. The body fluid sample is analyzed with the help of the analyzing apparatus.

In accordance with a further aspect of the invention a method is provided for operating a system for the extraction and infusion of a body fluid, in particular a system for the extraction and infusion of blood, the system having fluid distribution device having an outer structural element at which several connection ports are formed and an inner structural element which, at least partially, is arranged within a seat in the outer structural element, is displaceable between positions and has a hollow space configured for the intake and discharge of a fluid, wherein at the fluid distribution device a first connection port as a patient-side connection port, a first assigned connection port which is assigned to the first connection port as an infusion-side connection port and a second connection port as an analyzer-side connection port, wherein the method comprises the following steps:

arranging the inner structural element in a first position in which a bi-directional fluid connection through the hollow space is formed between the first connection port and the first assigned connection port with the hollow space being separated from the second connection port and a second assigned connection port which is assigned to the second connection port, introducing a body fluid sample through the first connection port into the hollow space, displacing the inner structural element to a second position in which the hollow space is in fluid connection with the second connection port, wherein the hollow space is separated from the first connection port and the first assigned connection port by of the arrangement of the inner structural element in the second position, at least partially discharging of the body fluid sample from the inner hollow space to a an analyzing apparatus through the second connection port, displacing the inner structural element to the first position, and providing an infusion fluid by means of an infusion apparatus to the first assigned connection port for discharge through the hollow space and the first connection port.

In a variant one step of the method can take the form of a flushing operation involving, for example, a physiological salt solution or an infusion solution by means of which the hollow space inclusive of the coupled connection ports in the selected position are rendered free of air, a situation in which air bubbles are avoided. The flushing stage can be carried out when the hollow space is connected to a connection port at each of its two ends so that the flushing fluid flows from one connection port to the other through the hollow space. However, an inflow and outflow of rinsing fluid through the same connection port can be provided if, for example, the hollow space set in the position for flushing being connected to only one connection port.

The proposed system provides the user with a simple means of extracting the body fluid sample by allowing the fluid to flow into the hollow space and then by positioning the inner structural element appropriately to pass all or part of the extracted body fluid sample through the second connection port. Flow through the first and the first assigned connection port can be achieved by using the bi-directional fluid connection through the hollow space of the fluid distribution device, a feature which is useful in extracting a body fluid or infusing a fluid by means of the system for extracting and infusing body fluids whereby, depending on the direction of flow, a body fluid may be extracted or an infusion fluid may be introduced. When infusion takes place this does not necessarily mean introducing an infusion liquid for therapeutic purposes, even if the fluid distribution device is useful in such a situation. Rather, a fluid can be fed into the fluid distribution device in order to flush residues of the body fluid back into the body.

When extracting a sample of a body fluid, for example a blood sample, from a patient it is possible to apply reduced pressure to the first assigned connection port which generates a suction to aid the collection method and causes the body fluid to flow into the hollow space. High demands for sterility can be satisfied in this way since in neither this position nor in the second position is there a fluid connection between the first connection port and the second connection port. In the positions, the hollow space in which the body fluid is collected is in fluid connection with only one of the connection ports. A direct flow between the connection ports is thereby effectively restricted whereby an effective barrier between the connection ports is formed.

In one possible variant, the inner structural element with the hollow space can be manufactured from solid material such that in a simple version a drilled hole is introduced in the hollow space. Another version provides that the inner structural element takes the form of an injection-molded component so that to at least a partial extent the hollow space structure is generated by a tool and in which a plastic material is introduced at the time of manufacture.

In one variant, when the system is in use the hollow space can be pressurized through the second assigned connection port which can serve, in particular, to force the fluid sample out of the hollow space through the second connection port. For example, the application of pressure can be used to feed the fluid sample to the analyzing apparatus.

A development of the invention provides that a channel system is formed in the inner structural element with the hollow space. In a simple modification the channel structure takes the form of straight channel through the inner structural element, for example, as a drilled hole. The channel structure can be produced in almost any desired configuration and can be provided with one or several openings through which the body fluid sample may flow into or out of the hollow space.

One development of the invention provides that in a third position the hollow space is in fluid contact with a third connection port which is configured so that a function fluid can be fed into the hollow space with separation from the first connection port, the second connection port and the second assigned connection port. In the provision of the third connection port, preferably, the hollow space is in the first or second position it is separated therefrom.

A development of the invention can provide that the inner structural element can be dislocated with a rotating movement between the positions. An inner structural element suitable for this purpose has, for example, essentially the form of a cylinder arranged to fit perfectly inside a housing formed by the outer structural element. Depending on the cylindrical form of the inner structural element, the outer structural element can have an overall circular cross-section with the connection ports being formed on the peripheral outer surface.

A further development of the invention can provide that the inner structural element has a positive fit into the seat. The positive fit optimizes the protection against an unintended flow of the fluid between the first and second connection ports. For that reason the inner structural element is conveniently fitted such that the dislocation between the position and the next position can only be effected by overcoming friction forces with the result that an unintended dislocation between the positions, caused, for example, by vibration of the system or by accidental contact, is avoided. In this way, the level of operational safety is increased.

An embodiment of the invention provides that the first position and the second position are adjacent positions of the inner structural element. For example, the first position and the second position are two adjacent rest positions of the inner structural element inside the external structural element. The different dislocation positions of the inner structural element are, for example, characterized in that in each of them there is a fluid connection between the hollow space and any connection port formed in the external structural element.

In a development of the invention, it can be provided that in intermediate positions which differ from the first and second positions the hollow space is formed as a connection-free hollow space. In an embodiment these intermediate positions are positions in the inner structural element in which, however, the hollow space cannot come into fluid connection with one of the connection ports formed in the outer structural element. In other words, in these intermediate positions it is not possible for fluid to either flow into the inner space or flow out of it. In one embodiment, this effect can be purposefully achieved by providing that in an intermediate position an opening providing access to the hollow space is always closed off by a portion of the surface of the outer structural element. In a convenient manner in a further development, the opening is in contact with surrounding portions of the inner structural element and assigned portions of the surface of the outer structural element. This further optimizes the sealing of the hollow space.

In an effective development of the invention, it can be provided that the hollow space can be dislocated between the first and second positions in a connection-free manner. This means that while the hollow space is located between the positions as a result of third intermediate location it has no fluid access to a connection port. Furthermore, it can be provided that the establishment of a fluid connection between the hollow space and a connection port as a consequence of repositioning the inner structural element only occurs if the fluid connection of the hollow space with the connection port open to the hollow space is first completely interrupted. In particular, this inhibits any possibility of contamination of the fluid in the hollow space. In a supplementary or alternative way it can be provided that the hollow space can be dislocated in a connection-free manner between the second and third positions and/or between the first and third positions passing through the intermediate positions.

A further development of the invention provides that in the third position the hollow space is in fluid contact with a third assigned connection port which is assigned to the third connection port and whereby a bi-directional fluid connection is established through the hollow space between the third connection port and the third assigned connection port. In this way a through-going fluid connection is created between the third connection port and the third assigned connection port such that a function fluid may flow in one flow direction or the opposite direction through the hollow space between the third connection port and the third assigned connection port.

In the case of developments of the method to operate the system for the collection and infusion of body fluids in accordance with the dependent sub-claims the explanations made in connection with the foregoing characteristics apply. Dependent upon the particular application situation, further developments of the method relating to the use of the distribution device and tubing systems which can optionally be connected can be provided which make use of the constructive development and connection possibilities of the distribution device.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE DRAWINGS

In order that the invention may be more readily understood, reference is made to the following examples, which are intended to illustrate the invention, but not limit the scope thereof. There follows below a more detailed description of a system for the collection and infusion of body liquids with a fluid distribution device referring to FIGS. 1 to 7. The same reference numbers are used throughout for similar features.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Figure 1:
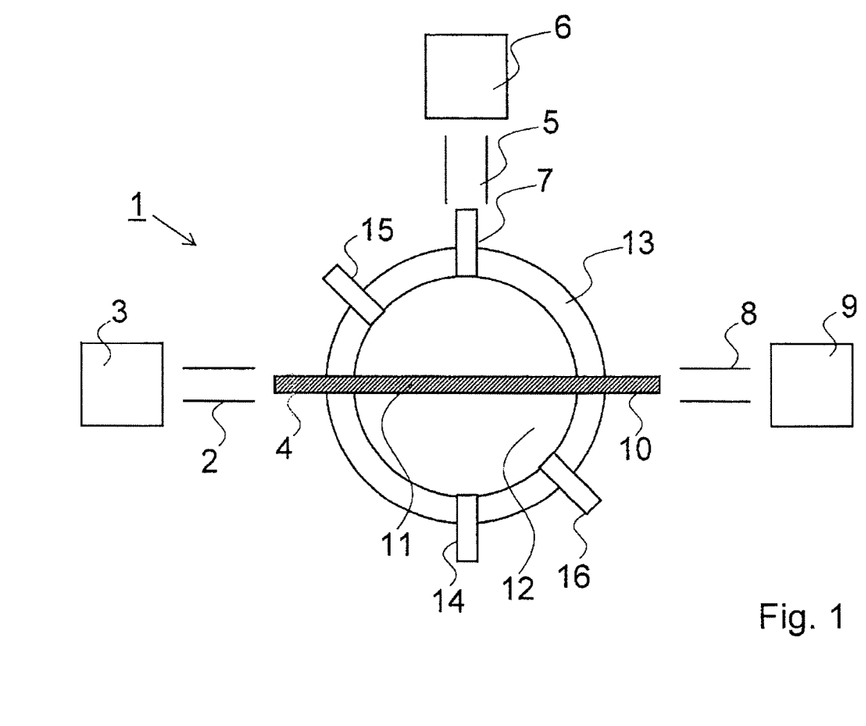
FIG. 1 is a schematic representation of a system for the collection and infusion of body fluids having a fluid distribution device where a fluid connection is made between a first connection port and a first assigned connection port.

FIG. 1 is a schematic representation of a fluid distribution device 1 by means of which a body fluid and, in particular, blood can be distributed in the system provided with several sets of fluid distribution tubing. In accordance with the schematic representation in FIG. 1 the patient-side fluid distribution system 2 is connected to a patient 3. The patient-side fluid distribution tubing 2 is connected to a first connection port 4. On the analyzer side, the fluid distribution device 1 is connected to an analyzing equipment 6 through fluid tubing 5 where the purpose of the analyzing equipment is to analyze a fluid, for example, blood supplied from the distribution device 1. The analyzer-side tubing system 5 is coupled to a second connection port 7. Furthermore, the fluid distribution device 1 as shown in FIG. 1 is coupled through an infusion-side distribution tubing system 8 to an infusion apparatus 9. This permits an infusion solution to be fed to the patient-sided tubing system 2 through the infusion sided tubing system 8, which is connected to a first assigned connection port 10, and then through a hollow space 11 formed itself in an inner structural element 12. If the direction of flow is reversed, a body fluid, for example, blood gains access to the patient 3 via the first connection port 4 in the hollow space 11.

According to FIG. 1 a second assigned connection port 14, a third connection port 15, and a third assigned connection port 16 are provided in an outer structural element 13 forming a housing in which the inner structural element 12 with the hollow space 11 is located in a pivotable manner. One or more of the connection ports, for example, the second assigned connection port 14 or the third connection port 15, can be placed downstream suitable preceding valves, particularly to permit the formation of separated circulations for different function fluids.

For example, the outer structural element 13 and the inner structural element 12 are made of plastic and produced by injection molding. The inner structural element 12 fits precisely in the outer structural element 13. Rotation of the inner structural element 12 against friction forces generated by assigned surfaces of the inner and outer structural elements 12/13 permits it to be brought to rest in different angular positions where, as shown in the embodiment represented by FIG. 1, the hollow space 11 is in fluid contact with different connection ports. When in an intermediate position (not illustrated), the hollow space is positioned in such a manner that there is no fluid connection to any one of the connection ports.

Figure 2:
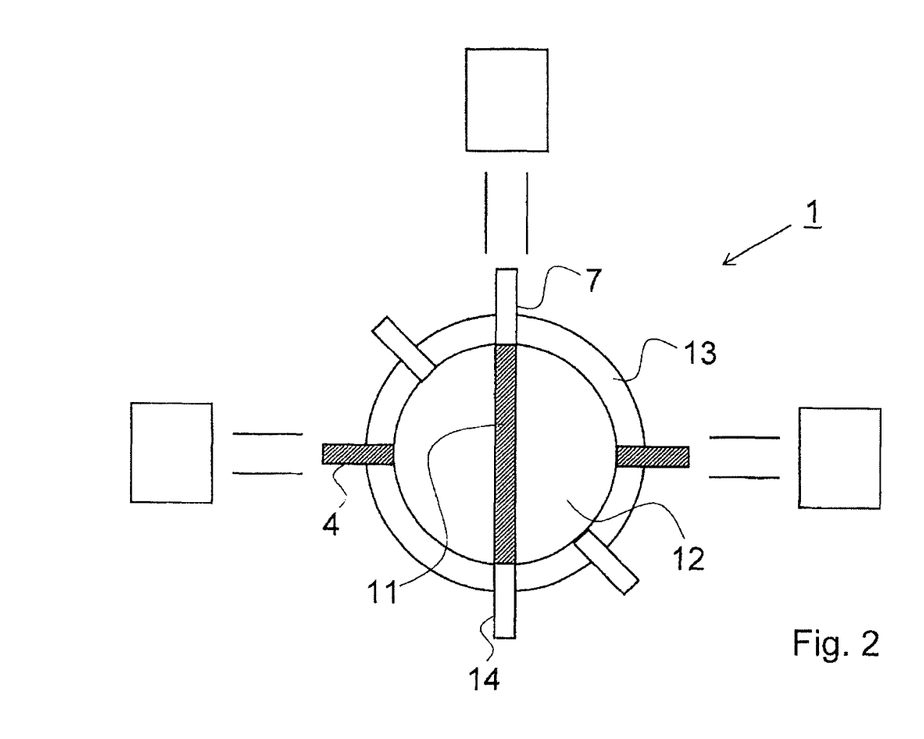
FIG. 2 is a schematic representation of system for the collection and infusion of body fluids as shown in FIG. 1 where a fluid connection is made between a second connection port and a second assigned connection port.
Figure 3:
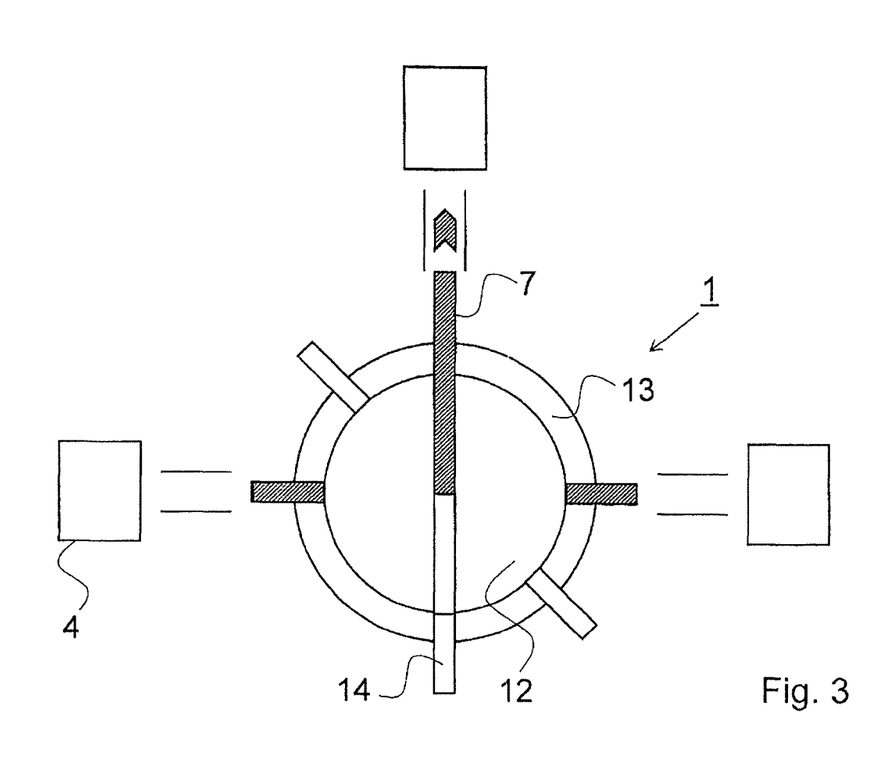
FIG. 3 is a schematic representation of a system for the collection and infusion of body fluids as shown in FIG. 2 where a sample of a body fluid is delivered through the second connection port.

FIG. 2 gives a schematic representation of the system for the collection and infusion of body fluids shown in FIG. 1 where the inner structural element 12 is brought by rotation to a dislocation position permitting a fluid connection between second connection port 7 and the second assigned connection port 14 to be made. After the dislocation position applied to the inner structural element 12 displayed in FIG. 1, a blood sample is fed into the hollow space 11, the blood sample can now be led through the second connection port 7 to the tubing system 5 and finally to the analyzing equipment 6 itself—particularly by means of pressurizing received through the second assigned connection port 14, as shown schematically in FIG. 3.

By using the illustrated position of the hollow space 11 shown in FIG. 2, which separates the hollow space 11 from the first connection port 4, function fluids may be introduced into the analytical equipment 6, for example, a calibration fluid to achieve calibration or a control fluid.

Figure 4:
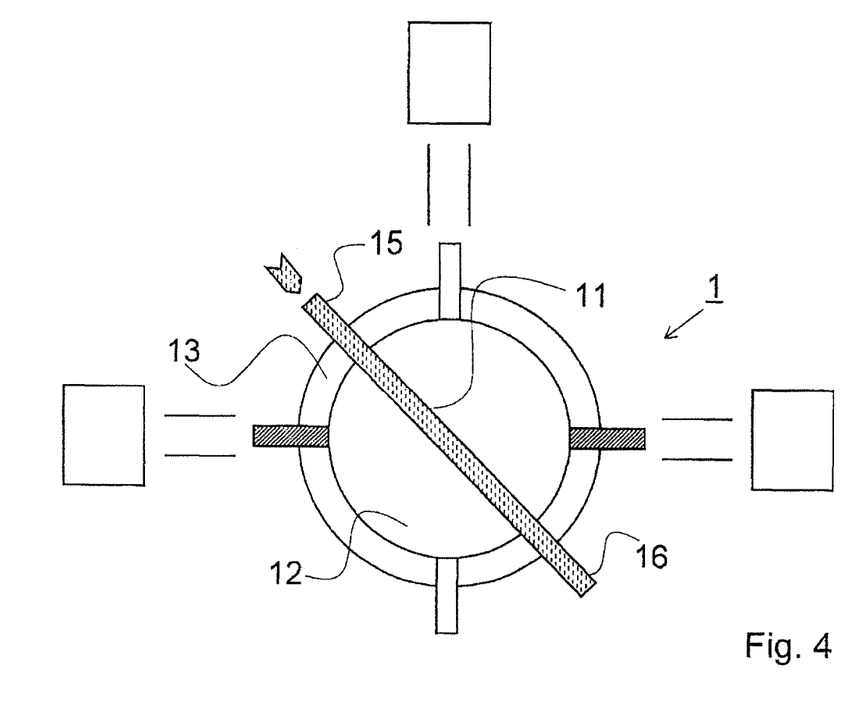
FIG. 4 is a schematic representation of a system for the collection and infusion of a body fluid as shown in FIG. 1 where a fluid connection is established between a third connection port and a third assigned connection port.

FIG. 4 gives a schematic representation of the system for the collection and infusion of body fluids as shown in FIG. 1, where now the inner structural element 12 has been brought into a dislocation position in which a fluid connection has been formed through the hollow space 11 between the third connection port 15 and the third assigned connection port 16. In this dislocation position, the inner structural element 12 finds itself in a cleaning position in which via the third connection port 15 a cleaning fluid can be introduced. Thus, the hollow space 11 is cleaned. Further there is the possibility of introducing a disinfecting solution. A cleaning—or washing solution can also introduced via the third connection port 15 (see position of the hollow space 11 in FIG. 2), which allows cleaning or flushing of the tubing system 5 of the analyzing equipment.

Figure 5:
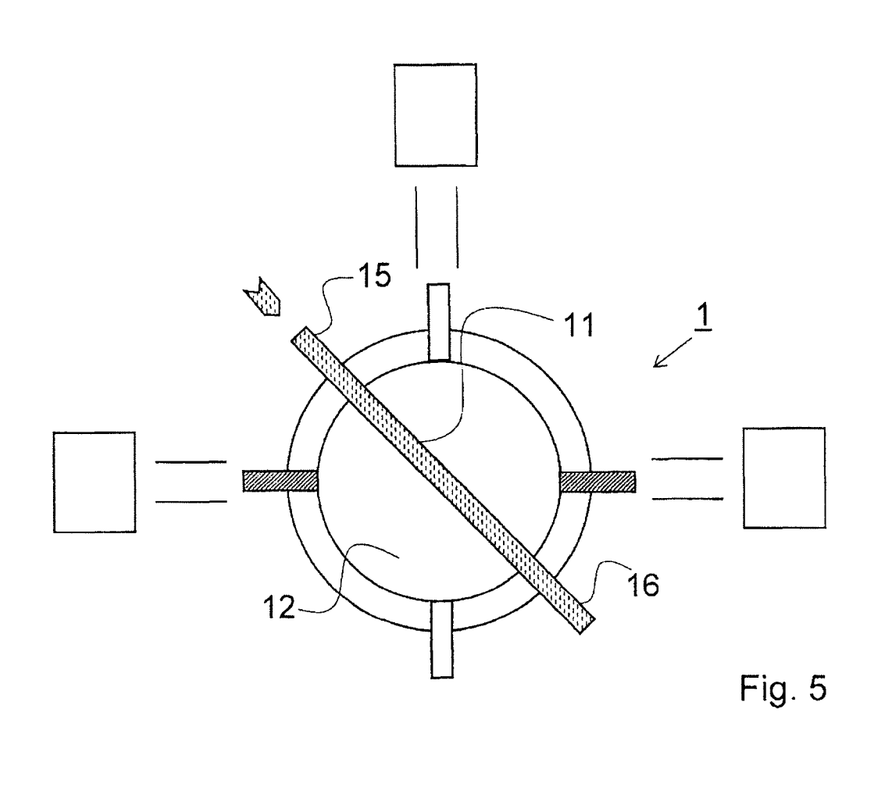
FIG. 5 is a representation of a system for the collection and infusion of body fluids as shown in FIG. 4 where an infusion liquid is introduced.

Finally, as is shown schematically in FIG. 5, the hollow space 11 is rinsed with infusion solution or a salt solution in order to avoid the presence of air bubbles in the infusion channel. The introduction of the infusion solution can also serve to flush back into the body of the patient any residues of the body fluid. In that case, the situation does not involve the use of an infusion liquid for therapeutic purposes, which can also be described as a rinsing liquid.

Figure 6:
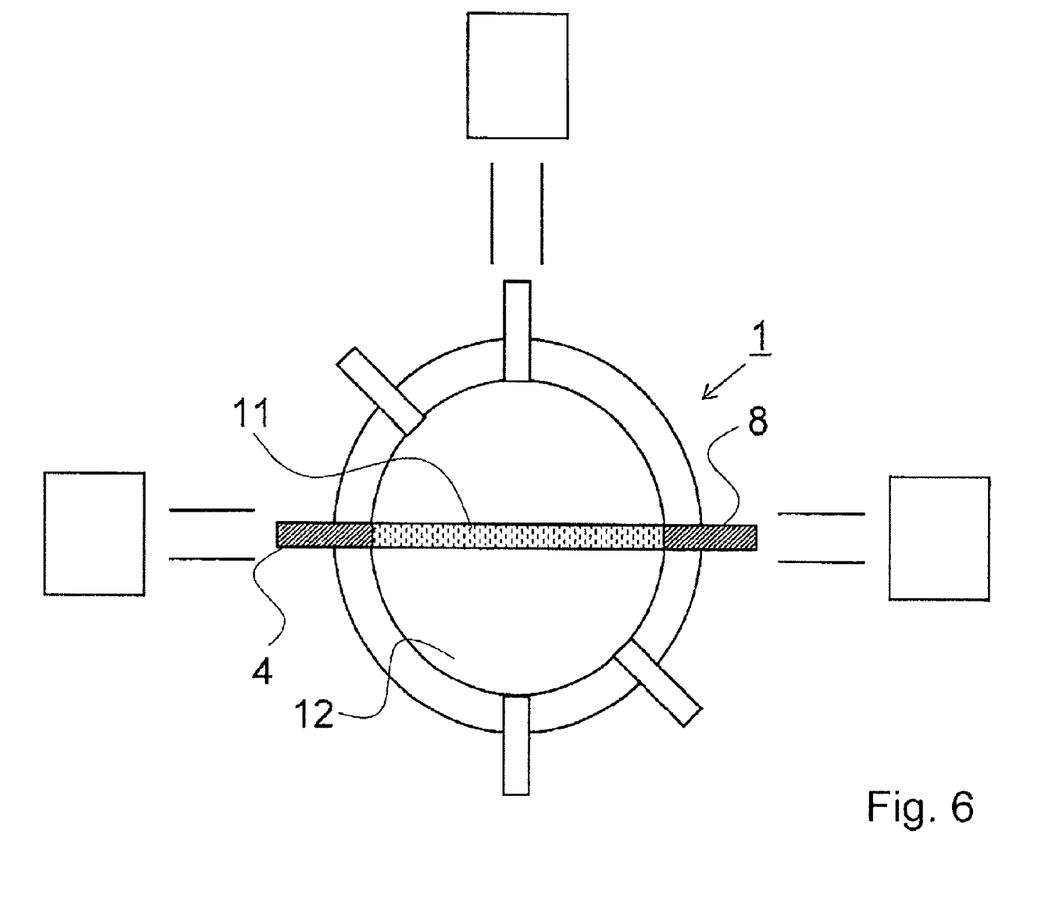
FIG. 6 is a schematic representation of a system for the collection and infusion of body fluids as shown in FIG. 5 where a fluid connection is established between the first connection port and the first assigned connection port.
Figure 7:
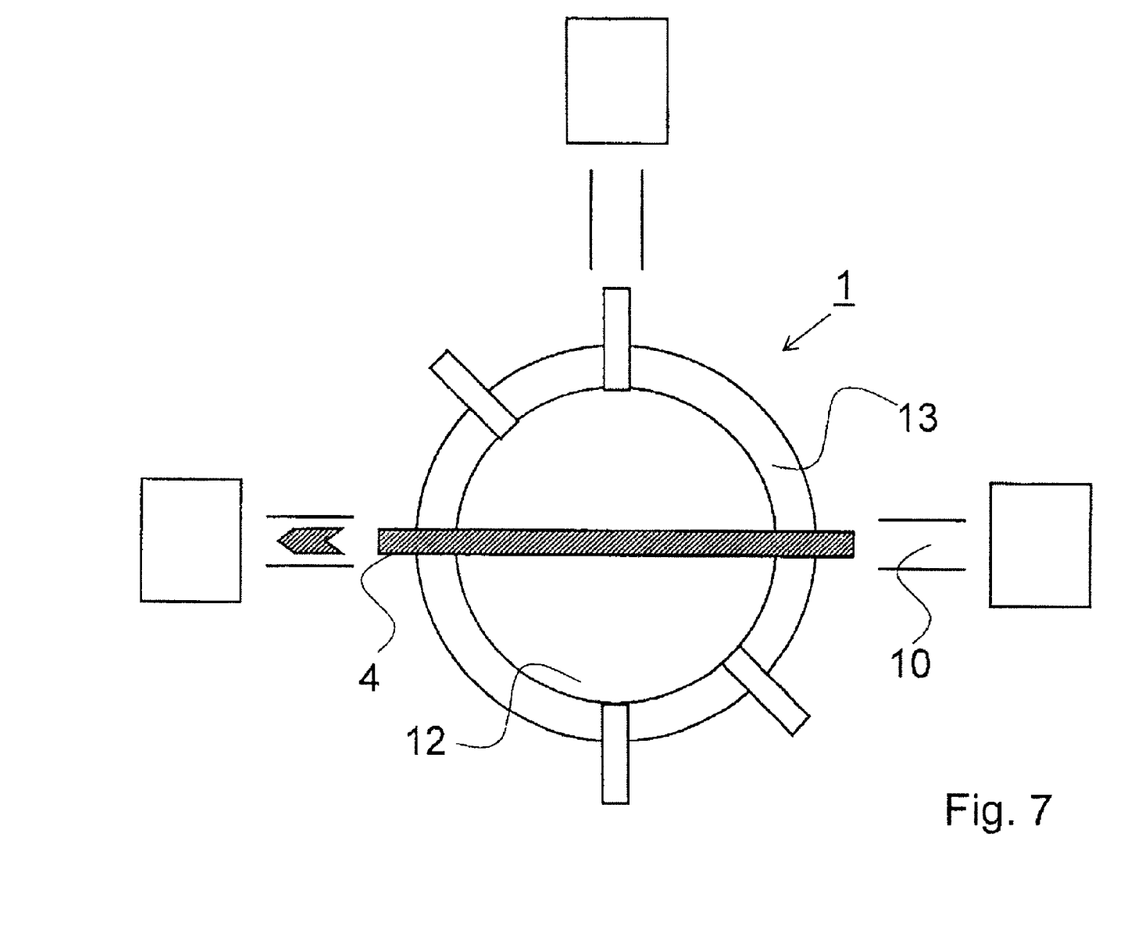
FIG. 7 is a schematic representation of a system for the collection and infusion of body fluids as shown in FIG. 6, where an infusion is made.

FIG. 6 then shows schematically how the hollow space 11, which has been filled with the infusion solution or the salt solution, is again provided with a fluid connection to the first connection port 4 and the first assigned connection port 10 to proceed with an infusion which is shown schematically in FIG. 7.

The fluid distribution device 1 in the system for the collection and infusion of body fluids displayed in FIGS. 1 to 7 can be used either in dependence on the foregoing embodiments described above or selectively in a different manner as described schematically in Table 1. There the appropriate reference numbers of the connection ports which are connected to the hollow space 11 are specified in the column headed "Position."

TABLE 1

| Step | Position | Action |
|---|---|---|
| 1 | 4-11-10 | Infusion fluid flows to patients through a length of distribution tubing 8-10-11-4-2. |
| 2 | 4-11-10 | Blood flows through the first connection port 4 into the hollow space 11. |
| 3 | | Movement of the inner structural element 12 to the Position 7-11-14. |
| 4 | 7-11-14 | Blood flows from the hollow space 11 through the second connection port 7 into the analyzing equipment 6, after which a measurement is made. After this, a function fluid, preferably air, flows through the second assigned connection port 14. |
| 5 | | Dislocation of the inner structural element 12 to the Position 15-11-16. |
| 6 | 15-11-16 | The hollow space 11 is cleaned with a washing fluid. This enters through the third connection port 15. Following the washing method, the washing liquid is replaced, preferably with air. |
| 7 | | Continue with Step 8 or Step 12. |
| 8 | 15-11-16 | Fluid present in the hollow space 11 is replaced by a further function fluid, such as, for example, a calibration- or QC-liquid (Control liquid). |
| 9 | | Movement of the inner structural element 12 to the Position 7-11-14. |
| 10 | 7-11-14 | Any function fluid in the hollow space 11 flows through the second connection port 7 and the analyzer-side tubing system 5 after which a calibration- or QC-measurement is made. |
| 11 | | Movement of the inner structural element 12 to the Position 15-11-16 followed by Step 8 or Step 12. |
| 12 | 15-11-16 | Fluid present in the hollow space 11 is replaced by infusion liquid. |
| 13 | | Movement of the inner structural element 12 to the Position 4-11-10. |
| 14 | 4-11-10 | Infusion liquid flows to the patient through the first connection port 4 and the patient-side distribution tubing system 2, when any residual liquid from Step 2 in the patient-side distribution tubing system 2, the first connection port 4, the first assigned connection port 10, and the infusion-side distribution tubing system 8 is flushed back into the body. |
| 15 | 4-11-10 | Continue with Step 1. |

One or more valves can be installed at the third connection port 15 so that optionally air or one of several function fluids can be introduced. If so desired, the washing liquid and the infusion liquid can be one and the same liquid. When initializing (operation) the explained arrangement with the fluid distribution device 1, normally, steps preceding step 1 are provided at this point, of which no further details can be given. For decoupling of the explained arrangement no further details can be given in regard to the steps following Steps 1 to 15.

Figure 8:
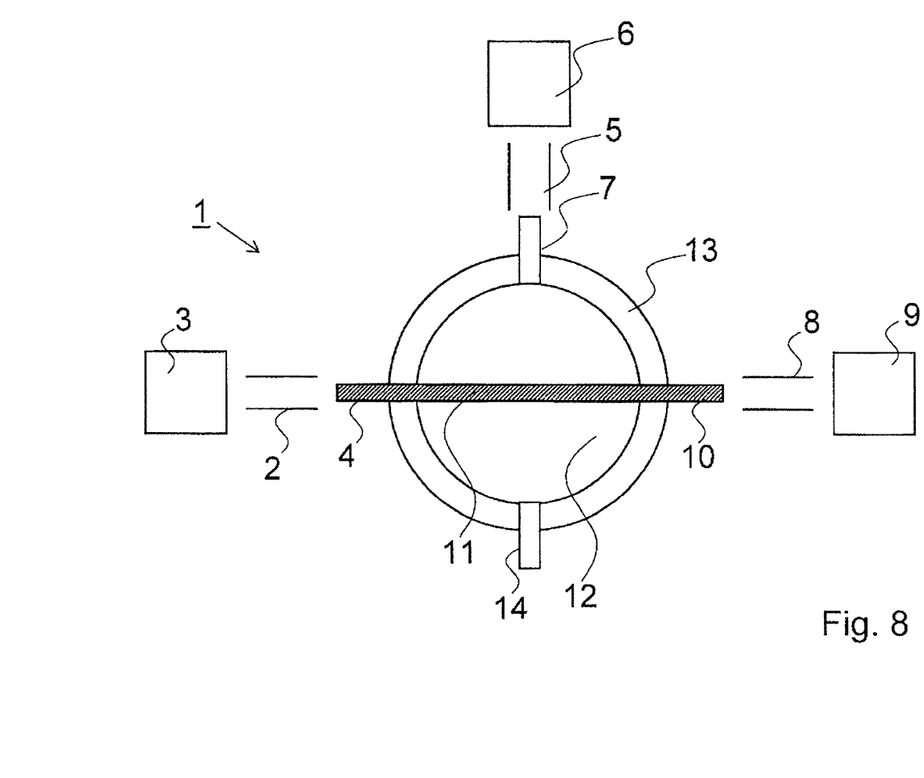
FIG. 8 is a schematic representation of a system for the collection and infusion of body fluids as shown in FIG. 1 where a reduced number of connection ports is available.

FIG. 8 shows a schematic representation of a fluid distribution device 1 with a reduced number of connection ports available. The fluid distribution device 1 seen in FIG. 8 can be operated in the manner described schematically in Table 2. Once again the appropriate reference numbers associated with the connection ports connected to the hollow space are given in the column headed "Position".

TABLE 2

| Step | Position | Action |
|---|---|---|
| 1 | 4-11-10 | Infusion liquid flows to patient through a section of the distribution tubing system 8-10-11-4-2. |
| 2 | 4-11-10 | Blood flows through the first connection port 4 into the hollow space 11. |
| 3 | | Dislocation of the inner structural element 12 to Position 7-11-14. |
| 4 | 7-11-14 | Blood flows from the hollow space 11 through the second connection port 7 into the analyzing equipment 6, after which a measurement is made. After that a function fluid, preferably air, flows through the second assigned connection port 14. |
| 5 | 7-11-14 | A section of the distribution tubing system 14-11-7-5 is cleaned with a washing liquid. This washing liquid flows in through the second assigned connection port 14, or through the analyzer-sided tubing system 5. Following the washing method, the washing liquid is replaced, preferably by air. |
| 6 (Optional) | 7-11-14 | One or more further function fluids are sequentially introduced through the second assigned connection port 14, if necessary separated by slugs of air, and flow through a section of the tubing system 14-11-7 to the analyzing equipment 6, after which calibration- or QC measurements are made. |
| 7 | 7-11-14 | Any function fluid or air arising from Step 5 or Step 6 is replaced by an infusion liquid. |
| 8 | | Move the inner structural element 12 to Position 4-11-10. |
| 9 | 4-11-10 | Infusion liquid flows to the patient so that any residual fluid in the patient-side tubing system 2 arising from Step 2, in the first connection port 4, the first assigned connection port 10, and the infusion-side distribution tubing system 8 connected connection port 8 is flushed back into the body. |
| 10 | 4-11-10 | Continue with Step 1. |

One or more valves can be installed at the second assigned connection port 14 so that at choice air or one of several function liquids can be introduced. If so desired the washing liquid and the infusion liquid can be one and the same liquid. When initializing (operation) the explained arrangement with the fluid distribution device 1, normally, steps preceding step 1 are provided at this point, of which no further details can be given. For decoupling of the explained arrangement no further details can be given in regard to the steps following Steps 1 to 10.

Figure 9:
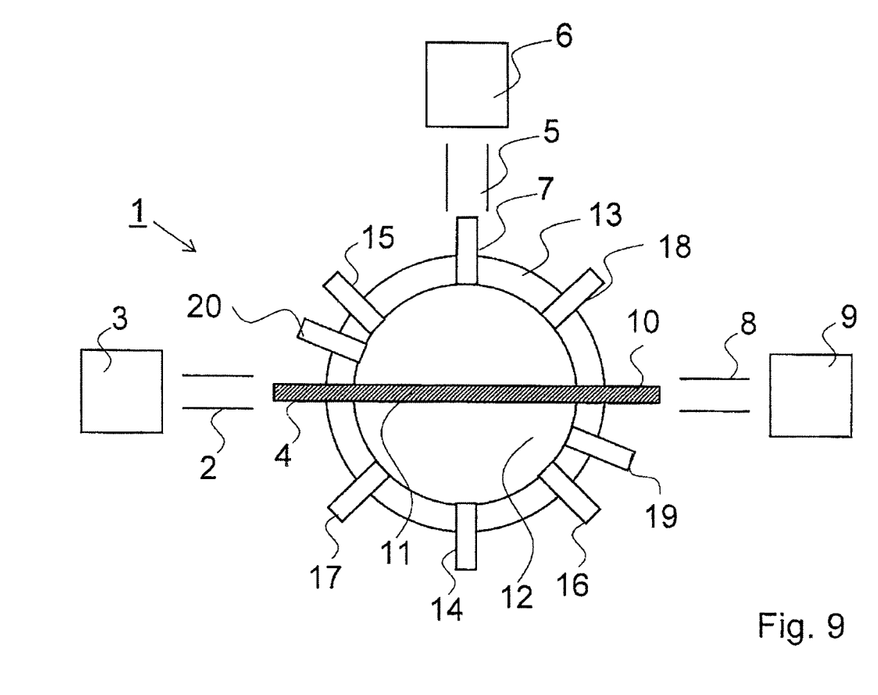
FIG. 9 is a schematic representation of a system for the collection and infusion of body fluids as shown in FIG. 1 where additional connections assigned to one another are provided.

FIG. 9 shows a schematic representation of the system for the collection and infusion of body fluids in accordance with FIG. 1, where additional connection ports 17, 18 and 19, 20 are assigned to one another. By making use of the additional connection ports assigned between one another it is possible to realize further separate circulations.

The operation cycles of the different versions of the distribution device described above provide developments which may however be modified and adapted to serve other requirements arising from specific application situations.

The features of the invention disclosed in the preceding Description, Claims and Drawings can be of significance as individual items or in any chosen combination for the implementation of the invention in its different embodiments.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:

1. A system for the extraction and infusion of body fluids comprising:
 a fluid distribution device comprising:
  an outer structural element, the outer structural element having a seat formed therein and a plurality of connection ports, and
  an inner structural element partially arranged in the seat formed in the outer structural element, the inner structural element having a hollow space defined therein to intake and discharge fluid,
 a patient-side fluid distribution system coupled to a first connection port of the fluid distribution device, the patient-side fluid distribution system being configured to be connected to a patient,
 an infusion apparatus coupled to a first assigned connection port of the fluid distribution device, the infusion apparatus being operable to supply fluid to the patient via the fluid distribution device,
 a blood analysis device coupled to a second connection port of the fluid distribution device, the blood analysis device being operable to analyze blood received from the patient via the fluid distribution device, and
 a source of pressurized fluid coupled to a second assigned connection port of the fluid distribution device,
 wherein the inner structural element is movable to a plurality of positions, including:
  a first position where (i) the hollow space fluidly connects the first connection port to the first assigned connection port of the plurality of connection ports of the outer structural element such that bi-directional fluid flow is permitted between the patient-side distribution system and the infusion apparatus, (ii) the hollow space is separated from the second connection port and the second assigned connection port of the plurality of connection ports of the outer structural element, and a second position where (i) the hollow space fluidly connects the second connection port to the second assigned connection port such that bi-directional fluid flow is permitted between the blood analysis device and the source of pressurized fluid, and (ii) the hollow space is separated from the first connection port and the first assigned connection port.

2. The system of claim 1, wherein the hollow space of the inner structural element is a channel structure.

3. The system of claim 1, wherein the inner structural element is movable to a third position where:
(i) the hollow space is fluidly connected with a third connection port configured to advance a function fluid into the hollow space, and
(ii) the hollow space is separated from the first connection port, the first assigned connection port, the second connection port, and the second assigned connection port.

4. The system of claim 3, wherein the hollow space is separated from the third connection port when the inner structural element is placed in the first position.

5. The system of claim 4, wherein the hollow space is separated from the third connection port when the inner structural element is placed in the second position.

6. The system of claim 1, wherein the inner structural element is moveable between the plurality of positions by a rotary movement.

7. The system of claim 6, wherein the inner structural element and the seat of the outer structural element have a positive fit.

8. The system of claim 6, wherein the first position and the second position are adjacent positions of the inner structural element.

9. The system of claim 1, wherein the inner structural element has a plurality of intermediate positions where the hollow space is separated from any of the plurality of connection ports of the outer structural element.

10. The system of claim 9, wherein one of the plurality of intermediate positions is located between the first position and the second position.

* * * * *

UNITED STATES PATENT AND TRADEMARK OFFICE
CERTIFICATE OF CORRECTION

PATENT NO.        : 8,444,594 B2                                                          Page 1 of 1
APPLICATION NO. : 12/680010
DATED             : May 21, 2013
INVENTOR(S)       : Gerd Schweiger It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 562 days.

Signed and Sealed this
Eighth Day of September, 2015

Michelle K. Lee
*Director of the United States Patent and Trademark Office*